(12) United States Patent
Dal Molin et al.

(10) Patent No.: US 8,150,517 B2
(45) Date of Patent: Apr. 3, 2012

(54) ACTIVE IMPLANTABLE MEDICAL DEVICE WITH RF TELEMETRY AND SUBCUTANEOUS ECG ELECTRODES

(75) Inventors: Renzo Dal Molin, Chatillon (FR); Anissa Bourguiba, Paris (FR)

(73) Assignee: Ela Medical S.A., Montrouge (FR)

( * ) Notice: Subject to any disclaimer, the term of this patent is extended or adjusted under 35 U.S.C. 154(b) by 695 days.

(21) Appl. No.: 11/551,626

(22) Filed: Oct. 20, 2006

(65) Prior Publication Data
US 2007/0106335 A1    May 10, 2007

(30) Foreign Application Priority Data
Oct. 21, 2005  (FR) ...................................... 05 10738

(51) Int. Cl.
*A61N 1/08*  (2006.01)
(52) U.S. Cl. ......................................................... 607/36
(58) Field of Classification Search .................. 607/32, 607/36, 60, 37; 600/508, 509, 510
See application file for complete search history.

(56) References Cited

U.S. PATENT DOCUMENTS

| | | | | |
|---|---|---|---|---|
| 5,078,134 A * | 1/1992 | Heilman et al. | ............... | 607/4 |
| 5,313,953 A * | 5/1994 | Yomtov et al. | ............... | 600/508 |
| 5,331,966 A * | 7/1994 | Bennett et al. | ............... | 600/508 |
| 5,861,019 A * | 1/1999 | Sun et al. | ............... | 607/60 |
| 6,115,630 A * | 9/2000 | Stadler et al. | ............... | 600/521 |
| 6,128,526 A * | 10/2000 | Stadler et al. | ............... | 600/517 |
| 6,144,879 A * | 11/2000 | Gray | ............... | 607/20 |
| 6,496,715 B1 * | 12/2002 | Lee et al. | ............... | 600/424 |
| 6,512,940 B1 * | 1/2003 | Brabec et al. | ............... | 600/374 |
| 6,522,915 B1 * | 2/2003 | Ceballos et al. | ............... | 600/509 |
| 6,577,893 B1 * | 6/2003 | Besson et al. | ............... | 600/509 |
| 6,631,290 B1 * | 10/2003 | Guck et al. | ............... | 600/509 |
| 6,766,190 B2 * | 7/2004 | Ferek-Petric | ............... | 600/512 |
| 7,215,991 B2 * | 5/2007 | Besson et al. | ............... | 600/509 |
| 2003/0135125 A1 * | 7/2003 | Lu et al. | ............... | 600/510 |
| 2004/0015199 A1 | 1/2004 | Thompson et al. | | |
| 2004/0215280 A1 | 10/2004 | Dublin et al. | | |
| 2004/0220625 A1 | 11/2004 | Silvestri et al. | | |
| 2005/0288600 A1 * | 12/2005 | Zhang et al. | ............... | 600/510 |
| 2006/0095083 A1 | 5/2006 | Zhang et al. | | |

* cited by examiner

*Primary Examiner* — Niketa Patel
*Assistant Examiner* — Hiba El-Kaissi
(74) *Attorney, Agent, or Firm* — Orrick Herrington & Sutcliffe, LLP

(57) ABSTRACT

An active implantable medical device with RF telemetry comprising subcutaneous ECG electrodes. The case (12) of the device comprises electrodes (20, 22, 24, 26) for collecting subcutaneous ECG signals coming into contact with the patient's tissues surrounding the case after implantation, as well as an RF telemetry antenna (30). These ECG electrodes are surface electrodes and the RF antenna is a surface antenna. The case (12) presents a significantly planar face (16) for mounting the ECG electrodes in an arrangement where these electrodes are significantly coplanar and spaced apart with each other, and receiving the surface RF antenna. A platelet (18) mounted onto the case comprises an insulating substrate comprising on its free face, conductive deposits (20, 22, 24, 26, 30) forming the ECG electrodes and the RF antenna.

9 Claims, 2 Drawing Sheets

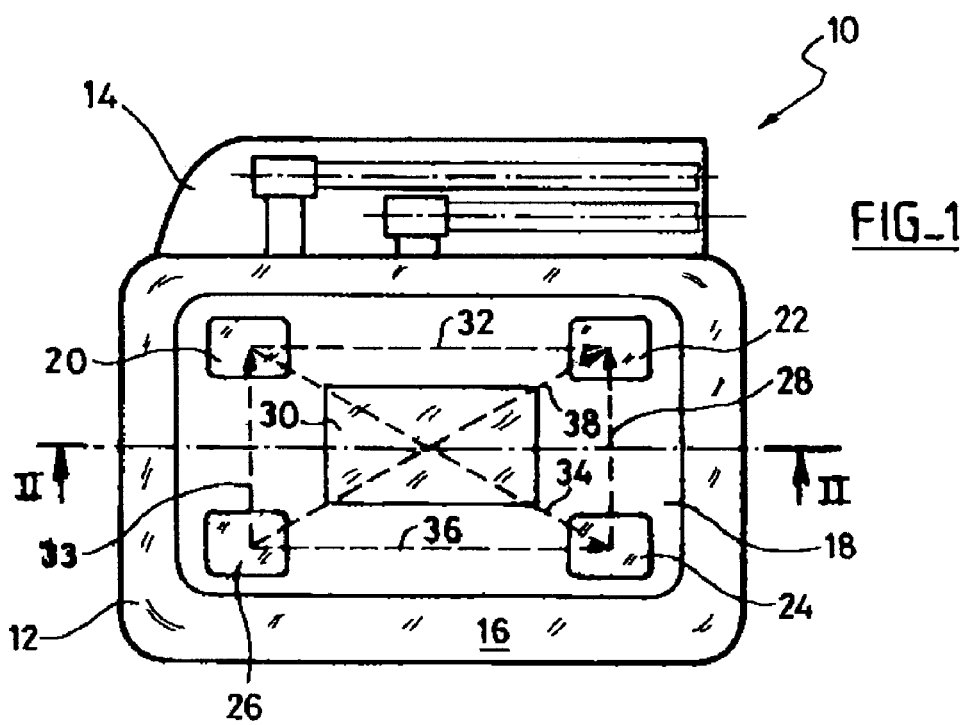
FIG_1
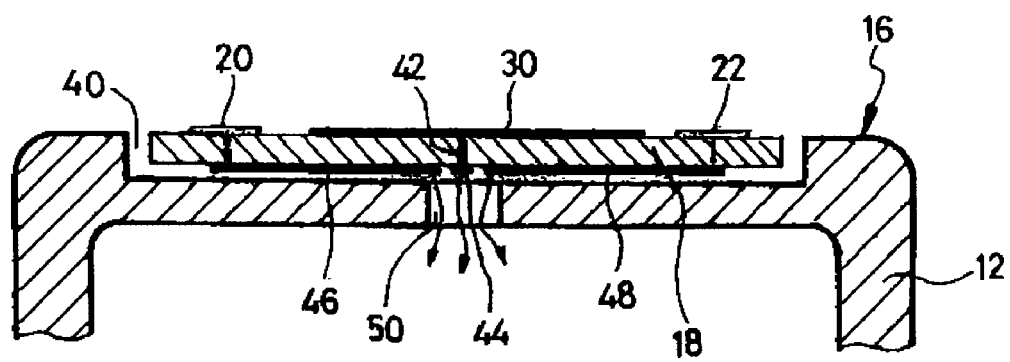
FIG_2
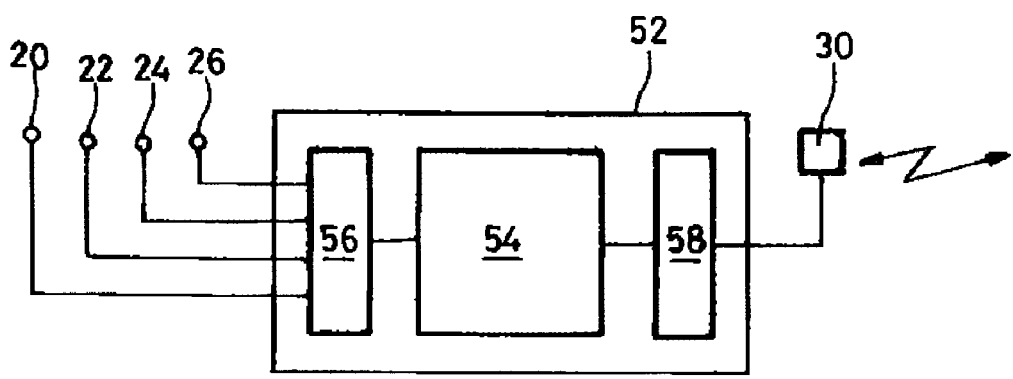
FIG_3

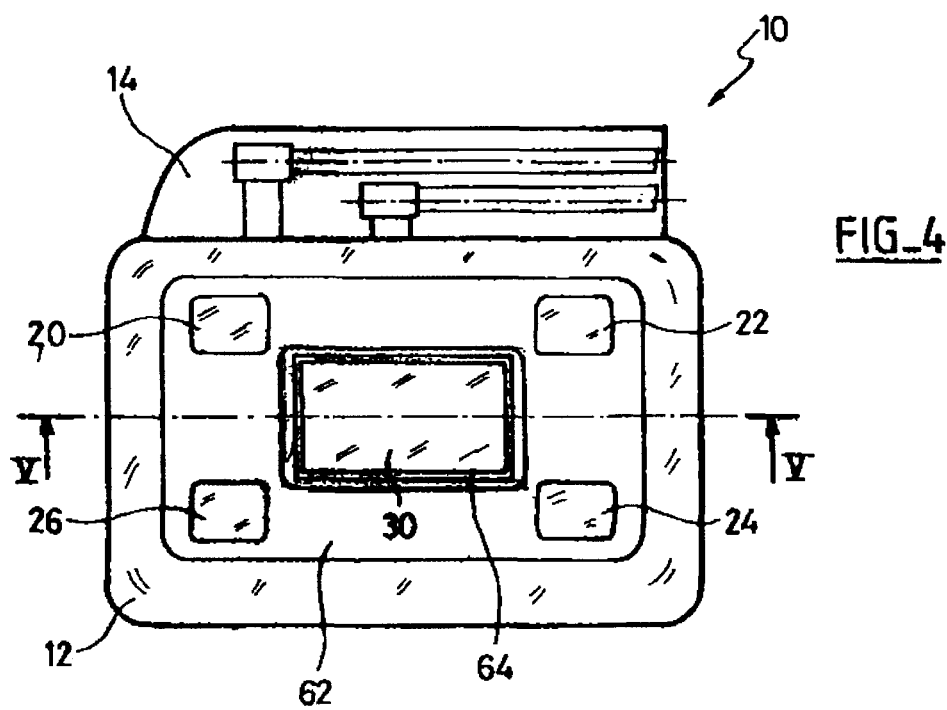
FIG_4
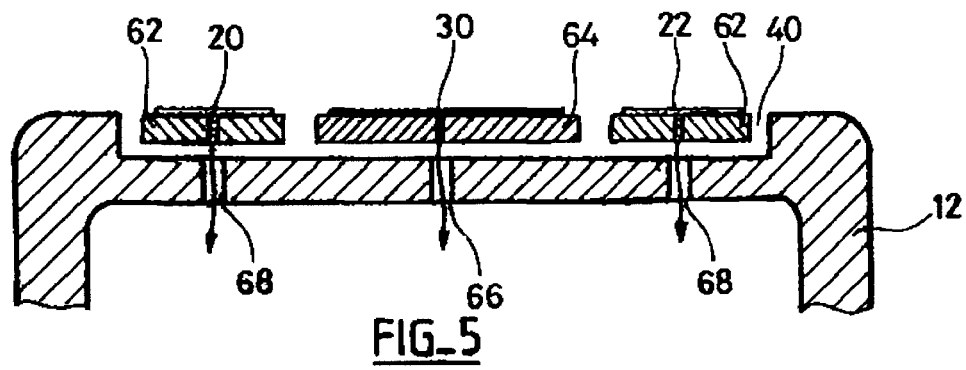
FIG_5
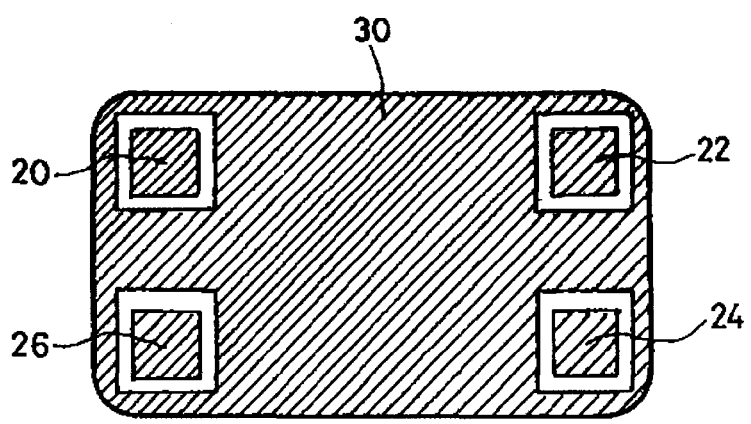
FIG_6

ACTIVE IMPLANTABLE MEDICAL DEVICE WITH RF TELEMETRY AND SUBCUTANEOUS ECG ELECTRODES

FIELD OF THE INVENTION

The present invention relates to "active implantable medical devices" as such devices are defined by the Jun. 20, 1990 Directive 90/385/CEE of the Counsel of the European Community, and more particularly to devices that continuously monitor heart rhythm and eventually deliver to the heart electrical pulses for pacing, resynchronization, cardioversion and/or defibrillation in cases of a rhythm disorder sensed by the device. The present invention more particularly concerns those devices, that collect subcutaneous electrocardiogram (ECG) signals, that is: devices whose implanted case contains electrodes to directly collect these signals from within the body, without requiring use of surface electrodes applied on the skin as in traditional external ECG recorders.

BACKGROUND OF THE INVENTION

The collection of subcutaneous ECG signals is to be distinguished from collection of electrogram (EGM) signals. The latter requires the use of intracardiac leads implanted in the myocardium, for the measurement of a depolarization potential, mainly for the purpose of controlling a cardiac stimulator. As for the ECG signals, they are intended to be recorded over a relatively long period of time, so as to be further processed and analyzed using reconstruction algorithms to assess the patient's clinical status, and eventually diagnose a heart rhythm disorder.

In the case of collecting subcutaneous ECG signals, the collected data are accumulated in a memory of the implanted device. Then, so as to allow them to be analyzed, the memorized data are transferred from the implanted device to an external device, or "programmer", that functions to verify the parameterization of the implanted device, read the recorded information or write data, and/or update the internal software of the implanted device.

That data exchange can be performed through telemetry, that is: through a technique of remote data transmission with no galvanic contact.

Up to now, telemetry used to be essentially performed through magnetic coupling between a coil of the implanted device and a coil of the programmer (or programming head), a technique known as an "induction technique". Recently, another non-galvanic coupling technique has been proposed, using the two components of an electromagnetic wave produced by transmitter/receiver circuits operating within the radiofrequency (RF) domain, typically with frequencies ranging around several hundreds of Megahertz. This technique, known as "RF telemetry", allows one to program or interrogate implanted devices from distances greater than 3 m, and therefore allows the exchange of data without the need for using a telemetry head, and indeed even without the intervention of an external operator.

U.S. Pat. No. 5,331,966 discloses an implanted device comprising electrodes for collecting subcutaneous ECG signals placed on its case, as well as means transmitting collected data using RF frequency towards an external device. The electrodes are positioned partly on the connector head, and partly on the case as such. Indeed, for a sufficiently efficient collection of the signals, the different electrodes shall be placed apart, as far away from each other and in as much of an orthogonal configuration as possible. U.S. Pat. No. 5,331,966 also refers to placing the electrodes on the edge of the case.

The latter arrangement of electrodes is also referred to in U.S. Pat. No. 6,522,915, which refers to a mounting element in the shape of a surround shroud placed around the periphery of the case and having over its external surface, electrodes in the shape of spiral wires. The implanted device includes an RF telemetry antenna, either within the case or placed on the connector head.

The devices described in these prior art documents present a relatively complex and very specific structure, notably so as to take into account the electrodes placement, which is an essential point for a satisfactory collection of ECG signals.

When it comes to equip an existing model of an implantable device with features for subcutaneous ECG signal collection, these constraints impose a redesign of the case so as to embed the electrodes (as in U.S. Pat. No. 5,331,966 referred to above) or use a follower element dedicated to the collection of ECG signals (as in U.S. Pat. No. 6,522,915 referred to above).

Furthermore, if it is wished to implement an RF telemetry system, the arrangement of the antenna relative to the case is also critical in order to obtain a satisfactory radiation pattern, respecting the conductive character of the case's body. By comparison, the induction telemetry technique is a more robust technique which is far less sensitive to such issues.

This is the reason why RF antennas of implanted devices are commonly placed in the connector head, because an antenna enclosed in the metal case could not radiate in a satisfactory manner.

OBJECTS AND SUMMARY OF THE INVENTION

It is, therefore, an object the present invention to propose an improvement to known devices equipped with electrodes for subcutaneous ECG signals collection and RF telemetry, by use of a rationalized electrode arrangement which further comprises an RF antenna.

It is another object of the invention to propose an electrode and antenna arrangement that shall be easily adaptable to existing devices as far as hardware issues are concerned, and in particular which does not require a total revision of the case design.

As will be understood by a person of ordinary skill in the art, the configuration of the present invention presents a relatively simple structure from a technical viewpoint, therefore it is particularly advantageous from the viewpoint of production cost, and in addition is more versatile, that is: easily adaptable to the different types of existing models of implantable devices, with no need for any substantial modification with respect to the design, manufacturing and regulatory approval of the implantable device, for e.g., pacing, resynchronization, cardioversion and/or defibrillation.

Broadly, one aspect of the present invention is directed to an implantable device of the type described in U.S. Pat. No. 5,331,966 cited above, that is: an implantable device having case that includes a plurality of ECG electrodes for the collection of subcutaneous ECG signals, said electrodes being arranged on an external area of the case that will come into contact with the patient's tissues surrounding the case after implantation, and an RF telemetry antenna. The electronic circuits of the device comprise a circuit for processing of the collected subcutaneous ECG signals, coupled to the electrodes placed on the case, as well as an RF telemetry transmitter/receiver circuit.

Preferably, the ECG electrodes are surface electrodes, and the RF antenna is a surface antenna. In one embodiment, the case is a flattened case presenting at least one significantly planar face, and includes: a first mounting area, spreading over most of said planar face and receiving the ECG electrodes in such an arrangement that the ECG electrodes are significantly and substantially coplanar and spaced apart, and a second mounting area on the surface of the case for receiving the surface RF antenna.

Various additional advantageous characteristics that are optionally included in one or more embodiment of the present invention include the following:

The first and second mounting areas both exist on the same planar face of the case, with the first mounting area preferably being a peripheral area, and the second mounting area being a central location of the planar face;

The first mounting area is an area that is significantly rectangular in shape and the ECG electrodes are arranged in the vicinity of the respective corners of said rectangle;

The first and second mounting areas comprise at least one platelet that is mounted to the external planar face of the case, having at least an insulating substrate interposed between the platelet and the case, and comprising on its free face conductive deposits forming respectively said electrodes and RF antenna; the platelet may be a common platelet comprising both the set of ECG electrodes and the RF antenna; and the platelet may be made entirely of an insulating substance adhered or fastened to the conducting case.

The platelet preferably comprises connecting conductors on its face that is applied onto the case, as well as vias connecting to said connecting conductors, said conductive deposits (areas) forming ECG electrodes and RF antenna; more advantageously, the case comprises a feedthrough whose terminal ends at a point located underneath the platelet, and the connecting conductors therefore converge towards this feedthrough;

The case preferably comprises on its planar face, a recessed area with dimensions similar to those of the platelet (or platelets), so that it (or they) can be mounted in the recessed area in a flush-mounted manner.

BRIEF DESCRIPTION OF THE DRAWINGS

Further features, advantages and characteristics of the present invention will become apparent to a person of ordinary skill in the art in view of the following detailed description of the invention, made reference to the drawings annexed, in which same number references represent identical elements, and in which:

FIG. 1 is an elevation view of a device according to a first embodiment of the invention, showing different electrodes for subcutaneous ECG signal collection and RF telemetry antenna;

FIG. 2 is a non-scaled cross sectional view profile taken along line II-II of FIG. 1;

FIG. 3 is a schematic drawing showing the various functional blocks linked to the electrodes and antenna, of a device in accordance with the present invention.

FIGS. 4 and 5 are respectively similar to FIGS. 1 and 2, for a second embodiment of the invention; and FIG. 6 shows electrodes and antenna configuration in accordance with a third embodiment of the invention.

DETAILED DESCRIPTION OF THE INVENTION

One will now describe examples of preferred embodiments of a device in accordance with the present invention. The invention can notably be applied to implantable devices commercialized by ELA Medical, Montrouge, France. These known devices are equipped with programmable microprocessors, including circuits intended and able to acquire, format and process electrical signals collected by implanted electrodes and deliver electrical pulses to these electrodes. Implementing the features and functionality of the present invention into these devices is believed to be within the abilities of a person of ordinary skill in the art, and will therefore not be described in detail in this document.

With reference to the drawings, reference 10 represents an implantable device having a case 12 embedding the various electronic circuits, a battery for power supply of the device (not shown as not pertinent to the present invention), and a connector head 14 mechanically mounted and electrically connected to the case and comprising one or more housings likely to receive one or more sensing/pacing intracardiac leads implanted in the myocardium. Case 12 also includes circuitry for effecting communications by RF telemetry, as well as a circuit for collecting and processing subcutaneous ECG signals using a suitable number of vectors, which circuits are known to persons of ordinary skill in the art.

Case 12 is preferably a case comprising at least one significantly planar face 16 receiving, in a manner characteristic of the invention, one mounting platelet 18 comprising electrodes 20, 22, 24 and 26 for collecting subcutaneous ECG signals, and, in this embodiment, an RF telemetry antenna 30. ECG electrodes 20, 22, 24 and 26 are preferably surface or "patch" electrodes, i.e. each of them has an electrically conductive material likely to contact the patient's tissues at the location where the device is implanted. The shape of each of these "patches" and the manner in which they are formed is not critical. The shape can be round, square, etc., the determining parameter being the surface area of the patch, and that the various electrodes 20, 22, 24 and 26 are arranged on a common plane. The material may be formal as a deposit of electronically conducting material laid over the surface of case 12 or platelet 18, as the case may be.

In the first embodiment illustrated on FIG. 1, there are four ECG electrodes, respectively located at the four corners of platelet 18, which has a rectangular shape. Thus the configuration of the four electrodes is an orthogonal configuration, allowing to collect ECG signals following a plurality of vectors, up to 6 vectors 28, 32, 33, 34, 36 and 38 (shown in dashed arrows). By thus arranging the electrodes at the four corners of platelet 18, the distance spacing these electrodes apart is maximized, which is an important factor for a satisfactory collection of ECG signals.

In an alternative embodiment, a configuration with only 3 electrodes is used, in an orthogonal configuration with electrodes 20, 22 and 24 allowing to collect the information following three vectors 28, 32 and 34. Conversely, more than four electrodes can be used, but that would induce a greater complexity of the signal processing, due to the increasing number of produced ECG signals.

As to the RF antenna 30, it is also realized in the shape of a surface element (preferably a patch antenna), which can advantageously be located in the central area of platelet 18. Whereas the arrangement of the respective ECG electrodes is determining, as explained above, the location of the antenna is not critical, and the latter can be located elsewhere on the platelet, or even on another platelet mounted on the opposite face of the case.

In practice, platelet 18 is made of an insulating substrate, for example, alumina or an alumina-ferrite-titanium oxide composite. On the free (or exposed) face of this substrate, a metal deposition is realized, for example in platinum or platinum-iridium, defining the "patches" of the ECG electrodes 20, 22, 24 and 26 and the RF antenna 30 also referred to herein as a "deposit". Very advantageously, platelet 18 is placed and bonded at the fundus of a recessed area 40 formed as part of the plane face of case 12 in such a manner that the exposed surface of platelet 18 is seated at a level to be flush-mounted onto the case surface, with minimal and preferably no thickness discontinuity.

The connection of the electrodes and antenna to the circuits located as part of the case is ensured by use of vias 42, passing through the thickness of platelet 18 and passing to the opposite face, where they are connected to conductors such as conductors 44, 46, 48, converging towards a feedthrough 50 formed the thickness of case 12, from where the conductors can be connected to the various circuits of the device.

As shown schematically on FIG. 3, circuits 52 comprise, in addition to a processing module for signals 54, a circuit stage for signal collection 56 connected to the electrodes 20, 22, 24 and 26, and an RF transmission/reception circuit stage 58 connected to the antenna 30.

Case 12 is preferably a conductive case (usually made of titanium), which does not induce any difficulties insofar as the electrodes and antenna are elements external to the case and electrically insulated therefrom by ceramic substrate platelet 18. Moreover, metal case 12 may eventually be used as an indifferent electrode for the ECG signal sensing circuit.

In the second alternative embodiment illustrated by FIGS. 4 and 5, the common platelet 18 as illustrated in FIGS. 1 and 2 is replaced by two distinct mounting platelets 62 and 64: a first platelet 62 is dedicated to support the ECG electrodes 20, 22, 24, 26, and a second platelet is dedicated to support the RF antenna 30. So as to keep the same overall configuration as in the previous embodiment, platelet 64 can be dimensioned to be housed within a central recess or aperture of platelet 62. In that embodiment, the electrodes and antenna are connected to the internal circuits of the case through respective feedthroughs 66, 68, formed underneath the respective elements, electrodes or antenna.

FIG. 6 shows another possible arrangement of the electrodes and antenna in accordance with a third embodiment of the invention: the common platelet is mainly dedicated to the antenna 30, which thus spreads nearly over to the edges of the device, while the ECG electrodes 20, 22, 24, 26 are formed by cells located in the vicinity of the four corners of antenna 30, interior to the external outline of antenna 30—differently, for example, from the configuration shown in FIGS. 1 and 4, in which the electrodes are located outwardly of the external outline of antenna 30.

Finally, in connection with any of the embodiments, it should be understood that case 12 also can include an internal coil for inductive telemetry, in addition to the external surface antenna used for RF telemetry.

One skilled in the art will appreciate that the present invention can be practice by other then the embodiments disclosed herein, which are presented for purposed of illustration and not of limitation.

We claim:

1. An active implantable device, of the pacing, resynchronization, defibrillation and/or cardioversion type, comprising:
   a case housing electronic circuits and a power supply, and having a first external mounting area presenting at least one significantly planar face and a second external mounting area;
   a connector head externally mounted to the case;
   a plurality of ECG electrodes for collecting subcutaneous ECG signals, said plurality of ECG electrodes being surface electrodes located on said first mounting area and disposed to contact a patient's tissues surrounding the case after implantation;
   an RF telemetry antenna mounted on said second mounting area, said RF telemetry antenna being a surface antenna;
   the electronic circuits comprising a circuit for processing said subcutaneous ECG signals, coupled to said plurality of ECG electrodes, and an RF telemetry transmitter/receiver circuit coupled to said RF telemetry antenna, wherein:
   said first mounting area and said second mounting area comprise at least one platelet made of an insulating substrate having an exposed face and a mounting face; and
   wherein said case comprises on said at least one significantly planar face, a recess with dimensions corresponding to said at least one platelet so as to house said at least one platelet in said recess in a flush-mounted manner and wherein;
   said first mounting area extends over said at least one significantly planar face and receives the plurality of ECG electrodes with an arrangement in which said plurality of ECG electrodes are significantly coplanar and spaced apart from each other; and wherein:
   said mounting face being mounted on said at least one significantly planar face and said exposed face having conductive deposits forming respectively said plurality of ECG electrodes and said RF telemetry antenna.

2. The device of claim 1, wherein said at least one platelet is a single platelet comprising said plurality of ECG electrodes and said RF telemetry antenna.

3. The device of claim 1, wherein said at least one platelet comprises connecting conductors on said mounting face and vias connecting said connecting conductors to said conductive deposits forming the plurality of ECG electrodes and RF telemetry antenna.

4. The device of claim 3, wherein the case comprises a feedthrough having a terminal located on said mounting face, wherein said connecting conductors converge towards said feedthrough.

5. An active implantable device, of the pacing, resynchronization, defibrillation and/or cardioversion type, comprising:
   a case housing electronic circuits and a power supply, and having a first external mounting area presenting at least one significantly planar face and a second external mounting area;
   a connector head externally mounted to the case;
   a plurality of ECG electrodes for collecting subcutaneous ECG signals, said plurality of ECG electrodes being surface electrodes located on said first mounting area and disposed to contact a patient's tissues surrounding the case after implantation;
   an RF telemetry antenna mounted on said second mounting area, said RF telemetry antenna being a surface antenna;
   the electronic circuits comprising a circuit for processing said subcutaneous ECG signals, coupled to said plurality of ECG electrodes, and an RF telemetry transmitter/receiver circuit coupled to said RF telemetry antenna, wherein:
   said first mounting area and said second mounting area comprise at least one platelet made of an insulating substrate having an exposed face and a mounting face; and
   wherein
   said first mounting area extends over said at least one significantly planar face and receives the plurality of ECG electrodes with an arrangement in which said plurality of ECG electrodes are significantly coplanar and spaced apart from each other; and wherein:

said first mounting area and said second mounting area further comprise a first platelet and a second platelet each made of an insulating substance and having an exposed face and a mounting face, said mounting face being mounted on said at least one significantly planar face, said exposed surface of the first platelet having thereon conductive deposits forming the plurality of ECG electrodes, the exposed surface of the second platelet having thereon conductive deposits forming said RF telemetry antenna and wherein:

said case further comprises a recessed area having a dimension corresponding to the outer dimensions of said first platelet and said second platelet wherein said first platelet and said second platelet are received within said recessed area to be flush mounted with said case.

6. The device of claim 5 wherein said first platelet has an internal recess and said second platelet has a dimension that fits within said internal recess of said first platelet.

7. The device of claim 6 wherein said plurality of ECG electrodes and RF telemetry antenna are substantially coplanar.

8. The device of claim 5 wherein said at least one platelet further comprises connecting conductors on said mounting face and vias connecting said constructing connectors to said conduction deposits forming the plurality of ECG electrode and said RF telemetry antenna respectively.

9. The device of claim 8 wherein, said case further comprises a feedthrough having a terminal at said mounting surface of said at least one platelet wherein said connecting conductors converge towards said feedthrough.

* * * * *